US010240171B2

(12) United States Patent
Baets et al.

(10) Patent No.: US 10,240,171 B2
(45) Date of Patent: *Mar. 26, 2019

(54) PREPARATION OF LACTIC ACID AND/OR A LACTATE SALT FROM LIGNOCELLULOSIC MATERIAL BY SEPARATE SACCHARIFICATION AND FERMENTATION STEPS (71) Applicant: PURAC BIOCHEM BV, Gorinchem (NL)

(72) Inventors: Peter Johannes Marie Baets, Spijk (NL); David Sanchez Garcia, Rotterdam (NL); Willem Jacob Groot, Dordrecht (NL); André Banier De Haan, Best (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,125

(22) PCT Filed: Jul. 28, 2015

(86) PCT No.: PCT/EP2015/067260
§ 371 (c)(1),
(2) Date: Jan. 25, 2017

(87) PCT Pub. No.: WO2016/016235
PCT Pub. Date: Feb. 4, 2016

(65) Prior Publication Data
US 2017/0292133 A1 Oct. 12, 2017

(30) Foreign Application Priority Data
Jul. 28, 2014 (EP) .................... 14178812
Jul. 28, 2014 (EP) .................... 14178816

(51) Int. Cl.
C12P 7/56 (2006.01)
D21C 1/06 (2006.01)
D21C 3/02 (2006.01)
D21C 11/00 (2006.01)

(52) U.S. Cl.
CPC ............ C12P 7/56 (2013.01); D21C 1/06 (2013.01); D21C 3/02 (2013.01); D21C 11/0007 (2013.01); C12P 2201/00 (2013.01)

(58) Field of Classification Search
CPC .. C12P 7/56; C12P 21/06; C12P 13/04; C12P 2201/00; C12P 2203/00
See application file for complete search history.

(56) References Cited

U.S. PATENT DOCUMENTS

| 4,734,109 A | 3/1988 | Cox | |
|---|---|---|---|
| 2012/0276585 A1* | 11/2012 | Ren | C12P 7/10 435/43 |
| 2014/0287466 A1* | 9/2014 | Sanders | C12P 7/46 435/71.1 |

FOREIGN PATENT DOCUMENTS

| WO | 00/17378 A2 | 3/2000 |
|---|---|---|
| WO | 2005/074647 A2 | 8/2005 |
| WO | 2005/123647 A1 | 12/2005 |
| WO | 2008/148131 A1 | 12/2008 |
| WO | 2009/025547 A1 | 2/2009 |
| WO | 2010/063762 A2 | 6/2010 |
| WO | 2011/035027 A2 | 3/2011 |
| WO | 2011/080155 A2 | 7/2011 |
| WO | 2011/095631 A1 | 8/2011 |
| WO | 2013/025107 A1 | 2/2013 |
| WO | 2013/062407 A1 | 5/2013 |
| WO | 2013/093028 A1 | 6/2013 |
| WO | 2013/093047 A1 | 6/2013 |
| WO | 2013/117687 A1 | 8/2013 |
| WO | 2013/174911 A1 | 11/2013 |

OTHER PUBLICATIONS

Oct. 6, 2015 International Search Report issued in International Patent Application No. PCT/EP2015/067260.
Oct. 6, 2015 Written Opinion issued in International Patent Application No. PCT/EP2015/067260.
Fanran Kong et al; "Effects of Cell-Wall Acetate, Xylan Backbone, and Lignin on Enzymatic Hydrolysis of Aspen Wood;" Applied Biochemistry and Biotechnology; 1992; vol. 34-35; pp. 23-35.
Vincent S. Chang et al; "Fundamental Factors Affecting Biomass Enzymatic Reactivity;" Applied Biochemistry and Biotechnology; 2000; vol. 84-86; pp. 5-37.
Ann Herlevich Brennan et al; "High Temperature Acid Hydrolysis of Biomass Using an Engineering-Scale Plug Flow Reactor: Results of Low Solids Testing;" Biotechnology and Bioengineering Symp.; 1986; No. 17; pp. 53-70.

(Continued)

Primary Examiner — Maryam Monshipouri
(74) Attorney, Agent, or Firm — Oliff PLC (57) ABSTRACT A process for preparing lactic acid and/or a lactate salt via the fermentation of carbohydrates obtained from lignocellulosic material. In particular the process includes: a) treating a lignocellulosic material with an alkaline agent including a caustic magnesium salt in the presence of water to provide a treated aqueous lignocellulosic material; b) saccharifying the treated aqueous lignocellulosic material in the presence of a hydrolytic enzyme to provide a saccharified aqueous lignocellulosic material including fermentable carbohydrates and a solid lignocellulosic fraction; c) fermenting the fermentable carbohydrates in the saccharified aqueous lignocellulosic material by way of lactic acid producing microorganism in the presence of an alkaline agent including a caustic magnesium salt to provide an aqueous fermentation broth including a magnesium lactate; and d) isolating lactic acid and/or lactate salt from the fermentation broth; wherein the saccharification step b) and the fermentation step c) are performed as two separate steps.

17 Claims, 1 Drawing Sheet (56) References Cited

OTHER PUBLICATIONS

Alireza Esteghlalian et al; "Modeling and Optimization of the Dilute-Sulfuric-Acid Pretreatment of Corn Stover, Poplar and Switchgrass;" Bioresource Technology; 1997; 59; pp. 129-136. (77).

N.D. Hinman et al; "Preliminary Estimate of the Cost of Ethanol Production for SSF Technology;" Applied Biochemistry and Biotechnology; 1992; vol. 34/35; pp. 639-649.

Jan. 10, 2018 Office Action issued in Canadian Patent Application No. 2,956,387.

* cited by examiner

PREPARATION OF LACTIC ACID AND/OR A LACTATE SALT FROM LIGNOCELLULOSIC MATERIAL BY SEPARATE SACCHARIFICATION AND FERMENTATION STEPS

The instant invention relates to a process for preparing lactic acid and/or a lactate salt via the fermentation of carbohydrates obtained from lignocellulosic material.

Lactic acid is often manufactured via fermentation of carbohydrates by microorganisms. A common feature to all fermentation processes is the need to neutralise the acids excreted by the microorganisms. A drop in pH below a critical value, depending on the microorganism used in the process, could damage the microorganism's metabolic process and bring the fermentation process to a stop. Therefore, it is common practice to add a base in the fermentation media in order to control the pH. This results in the lactic acid produced being present in the fermentation media in the form of a lactate salt.

Commonly used carbohydrate sources include, for example, sucrose, starch and sugar syrup. It is, for instance, very expensive when refined sugars and starch are used as the fermentation feedstock. Lignocellulosic materials are widely available renewable carbon sources that have no competing food value, are less expensive and are therefore attractive alternative feedstock for obtaining lactic acid via fermentation. However, there is still a need in the art to improve the commercial scale fermentation of lignocellulosic biomass for lactic acid production.

Lignocellulose consists primarily of cellulose and hemicellulose (i.e. polysaccharides build-up of mainly fermentable carbohydrates such as hexose sugars and pentose sugars) which are embedded in a matrix of the phenolic polymer lignin. In order to derive fermentable carbohydrates from lignocellulose a lignocellulosic material can be subjected to saccharification by, e.g., hydrolytic enzymes. In order to enhance the accessibility of the polysaccharides for enzymatic hydrolysis a physical and/or chemical treatment of the lignocellulosic material may be performed beforehand.

When the liberated carbohydrates are to be subjected to fermentation, it is common in the art to perform saccharification and fermentation simultaneously.

WO 2009/025547 describes a method for the production of organic acid, including lactic acid, comprising pre-treatment of lignocellulosic biomass with an alkaline agent followed by simultaneous saccharification and fermentation (SSF). $Ca(OH)_2$, CaO, $NH_3$, NaOH, KOH and urea are specifically mentioned as alkaline agents that may be used.

WO 2013/062407 describes a process for the conversion of lignocellulose into an organic acid comprising an alkaline pre-treatment step and a fermentation step, wherein liquid phase obtained in the fermentation step is recycled to the alkaline pre-treatment step and/or the fermentation step. The pre-treated material is subjected to SSF in the presence of both a hydrolytic enzyme and a microorganism that is able to convert saccharides into organic acid.

It was found that conducting SSF, using a lignocellulosic material as substrate, suffers from high viscosity problems. Typically, in SSF at the beginning of the hydrolysis reaction, the lignocellulosic material is a solid present in the form of a thick slurry or a thick paste. This makes it very difficult to satisfactorily perform hydrolysis and fermentation at the same time.

It further turned out that the amount of lignocellulosic material which may be used in practice for simultaneous saccharification and fermentation (SSF) is relatively low (e.g. 10-15 wt. %). Consequently the amount of sugar made available by hydrolysis in SSF is also relatively low, thereby compromising the efficiency of lactic acid production.

It has now been found that performing hydrolysis and fermentation as two separate steps (SHF) in a system in the presence of a caustic magnesium salt, any solid lignocellulosic fraction that may be present after enzymatic hydrolysis may be removed without adversely affecting the yields of lactic acid production. The removal of the solid lignocellulosic fraction even has been found to significantly reduce the viscosity and residual solids of the fermentation feed, which on its turn has been found to improve fermentation.

Separate saccharification and fermentation further allows the concentration of the fermentation feed (e.g. by evaporation of water), e.g. after saccharification and prior to fermentation. If required, a concentrated feed can be more easily transported. Generally, the provision of a concentrated feed can translate into a more efficient fermentation method. Concentration may be preferably performed after removal of said solid lignocellulosic fraction.

These and other advantages of a process as described herein will become evident from the detailed description below.

The following is a brief description of the drawings in the present application.

Several aspects of the instant invention relate to a process for preparing lactic acid and/or a lactate salt comprising: a) treating a lignocellulosic material (e.g. a lignocellulosic material which may be pre-treated) with an alkaline agent comprising a caustic magnesium salt in the presence of water to provide a treated aqueous lignocellulosic material; b) saccharifying the treated aqueous lignocellulosic material in the presence of a hydrolytic enzyme to provide a saccharified aqueous lignocellulosic material comprising fermentable carbohydrates and a solid lignocellulosic fraction; c) fermenting the fermentable carbohydrates in the saccharified aqueous lignocellulosic material by means of a lactic acid producing microorganism in the presence of an alkaline agent comprising a caustic magnesium salt to provide an aqueous fermentation broth comprising a magnesium salt of the lactic acid; and d) recovering the lactic acid and/or a salt of the lactic acid from the fermentation broth; wherein the saccharification step b) and the fermentation step c) are performed as two separate steps.

A process as described herein may be used for the production of lactic acid and/or lactate salts via fermentation of carbohydrates derived from a lignocellulosic material. Exemplary lactate salts include salts with cations such as for example magnesium, calcium, sodium, potassium and ammonium, in particular magnesium and calcium and even more in particular magnesium. In several embodiments a process as described herein may be used for the production of magnesium, calcium, ammonium, sodium and/or potassium lactate, more in particular magnesium lactate. The lactate salts may be acidified to obtain the corresponding lactic acid or may be converted to obtain another lactate salt. For instance magnesium lactate may be directly converted to lactic acid or may be converted to, e.g., sodium lactate which on its turn can be converted to lactic acid.

The term lignocellulosic material as used herein refers to any source of lignocellulose. A lignocellulosic material generally is of biological origin and in particular of plant origin. Approximately 90% of the dry weight of most plant materials is stored in the form of cellulose, hemicellulose, lignin and pectin, with the remainder being constituted by proteins, ash and extractives such as non-structural sugars, nitrogenous materials, chlorophyll and waxes. For instance, lignocellulose is generally found in the stems, leaves, hulls, husks, and cobs of plants and in leaves, branches, and wood of trees.

As indicated above, lignocellulose consists primarily of cellulose and hemicellulose which are embedded in a matrix of lignin. Lignocellulose may comprise other polymeric carbohydrates such as pectin, and other minor components. Lignin is a phenolic polymer. Cellulose and hemicellulose are polysaccharides, also referred to as carbohydrate polymers, build-up of mainly fermentable carbohydrates. Fermentable carbohydrates other than those originating from cellulose and hemicellulose may also be present in the lignocellulosic material.

As used herein, the term "fermentable carbohydrates" refers to carbohydrates which can be fermented by lactic acid producing microorganisms. Generally, fermentable carbohydrates are C5 sugars, C6 sugars, soluble oligomers thereof (e.g. C12 sugars) and/or soluble polymers thereof. By C5 sugars and C6 sugars is meant saccharides with 5 and 6 carbon atoms respectively and by C12 sugars is meant saccharides with 12 carbon atoms (e.g. a disaccharide). The type of fermentable carbohydrates that a specific microorganism may ferment may vary and they are either commonly known to the person of ordinary skill in the art or are easily accessible in the published literature. Particular examples of common carbohydrates fermentable by lactic acid producing microorganisms, may include C5 sugars such as arabinose, xylose and ribose; C6 sugars such as glucose, fructose, galactose, rhamnose and mannose; and C12 sugars such as sucrose, maltose and isomaltose. The type of sugar that a specific microorganism is able to ferment is known to the skilled person.

A suitable lignocellulosic material may be selected from, e.g., agricultural residue (e.g. straw and bagasse), herbaceous material (e.g. grass, leaves and fruits), municipal solid waste, paper pulp, paper mill residue, waste paper, wood and forestry residue (e.g., palm fronds).

In several embodiments a lignocellulosic material may be obtained from agricultural crops, in particular selected from at least one of, e.g., corn, wheat and sugar cane. In several embodiments a lignocellulosic material may be obtained from trees, in particular selected from at least one of, e.g., aspen, eucalyptus, fir, pine, spruce, willow and oil palm (including oil palm fronds). In other embodiments, the lignocellulosic material may be an aquatic biomass. As used herein the term "aquatic biomass" means biomass produced in an aquatic environment by a photosynthetic process. An aquatic lignocellulosic material may be selected from, e.g., red algae, emergent plants, floating-leaf plants, and submerged plants.

A lignocellulosic material may be preferably selected from at least one of wood (hardwood or soft wood), corn residues (e.g. stover, cobs, and stalks), sugar cane residues (e.g. bagasse, tops and leaves), and straw (e.g. wheat straw, maize straw, barley straw, rice straw, rye straw).

A lignocellulosic material may be characterized by a cellulose and hemicellulose content from 30 to 99 wt. %, based on the dry weight of the material, in particular from 50 to 95 wt. %. A lignocellulosic material may be preferably characterized by a cellulose content of from 20 or 30 wt. % to 70 wt. %, based on the dry weight of the material.

A process as described herein comprises treating a lignocellulosic material with an alkaline agent comprising a caustic magnesium salt in the presence of water to provide a treated aqueous lignocellulosic material, herein also referred to as treated lignocellulosic material. For the purposes of the instant description, the treatment of the lignocellulosic material with the alkaline agent comprising a caustic magnesium salt is referred to as "alkaline treatment."

A lignocellulosic material may be used in any suitable form. A lignocellulosic material will generally be in solid form (e.g. a particulate or a paste) or in liquid form (e.g. a slurry in water).

A lignocellulosic material generally comprises water. Water present in the lignocellulosic material may generally be water naturally present in the lignocellulosic material. Alternatively or additionally, water may be added to the lignocellulosic material prior to and/or during a treatment with an alkaline agent as described herein.

For the purposes of the instant description an alkaline agent comprising a caustic magnesium salt is also referred to as "magnesium-containing alkaline agent", or simply as "alkaline agent". The alkaline agent may be added to the lignocellulosic material in solid form, in the form of an aqueous solution or in the form of an aqueous slurry (e.g. having the caustic magnesium salt partially dissolved in water and partially in solid form).

A caustic magnesium salt of an alkaline agent as described herein may be selected from at least one of magnesium oxide (MgO), magnesium hydroxide ($Mg(OH)_2$), magnesium carbonate ($MgCO_3$), magnesium hydrocarbonate ($Mg(HCO_3)_2$), alkaline magnesium silicate, trimagnesium phosphate, and mono-magnesium phosphate. Preferably, the caustic magnesium salt is selected from at least one of MgO, $Mg(OH)_2$, $MgCO_3$, and $Mg(HCO_3)_2$. More preferably, the caustic magnesium salt comprises MgO and/or $Mg(OH)_2$ The alkaline agent may comprise bases other than a caustic magnesium salt, such as a caustic sodium salt, a caustic potassium salt, caustic calcium salt and/or a caustic ammonium salt, such as NaOH, $Na_2CO_3$, $NaHCO_3$, KOH, $K_2CO_3$, $KHCO_3$, CaO, $Ca(OH)_2$, $CaCO_3$, $Ca(HCO_3)_2$, $NH_4OH$, $(NH_4)_2CO_3$, and $(NH_4)HCO_3$, in particular a caustic sodium salt and/or a caustic potassium salt, more in particular $Na_2CO_3$, NaOH, $K_2CO_3$, and/or KOH. The use of a caustic magnesium salt without said other caustic salts may be preferred. In particular, the alkaline agent may comprise predominantly a magnesium salt (e.g. more than 90 wt. %, 95 wt. %, preferably more than 98 wt. %, based on the total weight amount of alkaline agent) or even consist of solely a caustic magnesium salt. Accordingly, the alkaline agent may comprise or consist of at least one of MgO, $Mg(OH)_2$, $MgCO_3$ and $Mg(HCO_3)_2$. The alkaline agent may preferably comprise or even consist of MgO and/or $Mg(OH)_2$.

An alkaline treatment may be generally performed by adding a magnesium-containing alkaline agent to the lignocellulosic material and mixing the alkaline agent and the lignocellulosic material in the presence of water to provide a reaction mixture. Mixing may be performed by any suitable methods known in the art, e.g., at least one of agitation, stirring, liquid phase recirculation, by selecting an appropriate flow rate through a tubular reactor, or by using a screw conveyor, an extruder, a concrete grinder or trickle bed with liquid recirculation.

An alkaline treatment as described herein may be generally performed for a dry weight content of lignocellulosic material from 1 to 70 wt. %, based on the total weight of the reaction mixture (w/w), in particular from 1 to 70 wt. %, from 5 to 50 wt. %, more in particular from 10 to 30 wt. %.

The dry weight of lignocellulosic material may be determined prior to addition of the alkaline agent, by for instance, filtering a sample of the lignocellulosic material (e.g. with a glass microfiber filter paper), washing the filter cake with water, and drying the cake overnight. For instance: the lignocellulosic material may be heated in air at 105° C. to a constant weight, in accordance with ASTM E1756-08.

An alkaline treatment as described herein may be performed using an amount of caustic magnesium salt (excluding any other caustic salts present in the alkaline agent) of at least 0.1 wt. %, based on the dry weight of lignocellulosic material (w/w). If other bases are present in the alkaline agent in addition to the caustic magnesium salts, the amount of such other bases will be determined by the pH at which the alkaline treatment is performed and by the type of base used. A person skilled in the art knows which amounts of other bases to select depending on the targeted pH and depending on the additional bases of choice.

An alkaline treatment as described herein may be performed at a temperature from 15 to 250° C., in particular from 30 to 200° C. Temperatures higher than 250° C. have been found to result in undesired degree of degradation of the lignocellulosic material. Temperatures lower than 15° C. may be regarded as less suitable as they may require cooling without necessarily benefiting the process.

In several embodiments the temperature may be from 130 to 250° C., such as from 140° C. or from 170° C. to 200° C. Such temperatures have been found to particularly facilitate subsequent saccharification, in particular when using an alkaline agent comprising a caustic magnesium salt as described herein. A treatment at such high temperatures may be performed by increasing the temperature by direct addition to the lignocellulosic material of live steam (i.e. steam under pressure) or superheated steam, or by indirectly heating the lignocellulosic material.

In several embodiments the temperature may be from 15 to 100° C., in particular from 30 to 80° C., and more in particular from 45 to 70° C. Such temperatures may be desired, for instance, when the lignocellulosic material has been previously treated and/or when the alkaline treatment is performed as a neutralization step. In particular, if the lignocellulosic material has been previously subjected to high temperatures there may be no need for the alkaline treatment to be performed also at high temperatures.

An alkaline treatment as described herein may be performed for a time period from less than 1 minute to 600 minutes, in particular from 1 minute to 480 minutes, more in particular from 30 to 250 minutes, even more in particular from 60 to 150 minutes. The alkaline treatment may be performed for less than 1 minute. Preferred residence time will depend significantly upon the selected temperature, pH and type of lignocellulosic material as well as on the purpose of the alkaline treatment. For instance, selecting a higher temperature within the defined range can reduce the required residence time to achieve an effective hydrolysis. Analogously, operating at a higher pH within the recited range will also permit a reduced residence time. Alkaline treatments at ambient temperatures (e.g., temperatures from 15 to 45° C.) may also be performed for longer periods of time (for few weeks or few months), e.g., by soaking the lignocellulosic material in water comprising of a small amounts of the alkaline agent comprising a caustic magnesium salt. This may be performed, e.g., during storage of the lignocellulosic material.

The pH of an alkaline treatment as described herein may depend on the starting pH of the lignocellulosic material, the amount of alkaline agent used and the amount of acid that may be liberated during the treatment. The pH of the alkaline treatment may generally be from 4.0 to 14.0, in particular from 4.5 to 13.0, more in particular from 5.0 to 12.0.

In several embodiments the pH may be from 8.0 to 14.0, in particular from 8.5 to 13.0 and more in particular from 9.0 to 12.0. Such pH have been found to facilitate a subsequent saccharification. In several embodiments the pH may be from 4.0 to 9.0, in particular from 4.5 to 8.0.

Prior to or simultaneously with an alkaline treatment as described above, a lignocellulosic material may be subjected to additional treatments, such as a physical treatment (e.g. mechanical treatments such as comminuting, grinding, milling, refining, extrusion, pressing shear treatments and/or pressure wave treatments; thermal treatments such as heating; microwave treatments; ultrasound treatments; and pulsed electric field assisted treatments), physicochemical treatment (steam treatment such as steam explosion, ammonia fibre expansion (AFEX), wet explosion, hydro-thermolysis, and wet oxidation), a chemical treatment (e.g. with acids, oxidizing agents such as $H_2O_2$ or $O_2$, organic solvents or bases other than a caustic magnesium salt)and/or a biological treatment (e.g. with white root fungi).

In the context of a process as described herein, a treatment performed prior to a treatment with a magnesium-containing alkaline agent is referred to as a pre-treatment. A pre-treatment may be generally performed to break down the lignocellulosic material in order to, e.g., increase the accessible surface area of the lignocellulosic material, disrupt the cell wall components of the lignocellulosic material, dissociate lignin from cellulose and hemicellulose, increase the accessibility of hydrolytic enzymes to the polymeric carbohydrates in a subsequent saccharification step, and/or hydrolyse polymeric carbohydrates.

In several embodiments, a pre-treatment may comprise physical treatment. In particular, a physical treatment may preferably comprise a mechanical treatment to provide a comminuted lignocellulosic material. Comminuting may be performed by methods known in the art including, e.g., grinding, milling, and extrusion. Such a treatment advantageously increases the surface area of the lignocellulosic material making it accessible to subsequent treatments.

In several embodiments, a pre-treatment may comprise chemical treatment. In particular a chemical treatment may preferably comprise an acid treatment (acid hydrolysis) and/or a solvent treatment (e.g. extraction). For instance, a solvent may be used to dissolve lignin.

An acid treatment may comprise mixing a lignocellulosic material with an acidic aqueous solution which may include one or more of an inorganic acid, an organic acid, an amino acid, a mineral acid, a Bronsted acid and a Lewis acid. More usually, the acid may be hydrochloric acid, sulfuric acid, sulphurous acid (alone or in combination with bisulphite ion), sulfonic acid, phosphoric acid, nitric acid, acetic acid, lactic acid, formic acid, oxalic acid, succinic acid, levulinic acid, carbonic acid, glycolic acid, uronic acid, glucaric acid, hydrofluoric acid, boric acid, boron trifluoride, or any combination of these acids. Solutions containing acidic salts, such as aluminum sulfate, ferric sulfate, aluminum nitrate or ferric nitrate may also be useful. Hydrochloric acid, sulfuric acid, sulphurous acid (alone or in combination with bisulphite ion) and nitric acid may be preferred, and hydrochloric acid may be particularly preferred. In several embodiments, the acid treatment may be a sulphite treatment also known in the art as the sulphite process, whereby a mixture of sulphurous acid and bisulphite ion (e.g. calcium bisulphite) is used to degrade lignin.

Whilst concentrated acids may be powerful agents for cellulose hydrolysis, they are concomitantly toxic, corrosive and hazardous, and are therefore not preferred for use herein. Concentrated acids are also costly and hard to recover. Desirably therefore, when used, an aqueous acidic pre-treatment solution should have a concentration of less than 8 wt. %, for instance less than 4 wt. %. Such a dilute acid pre-treatment step may typically take place at a temperature of from 120 to 230° C. A person of ordinary skill in the art will of course be able to determine an appropriate contact or residence time, acid concentration and contact temperature for particular acids and ligncellulosic feedstocks. And the following teachings may inter alia be instructive in this regard: Esteghlalian, A. et al. *Modeling and optimization of the dilute-sulfuric-acid pretreatment of corn stover, poplar and switchgrass*, Bioresour. Technol. 1997, 59, 129-136. (77); Hinman, N. D. et al. *Preliminary estimate of the cost of ethanol production for SSF technology*, Appl. Biochem. Biotechnol. 1992, 34/35, 639-649; and, Brennan, A. H. et al. *High temperature acid hydrolysis of biomass using an engineering-scale plug flow reactor: Result of low solids testing*, Biotechnol. Bioeng. Symp. 1986, 17, 53-70.

A solvent treatment will generally comprise an extraction. As used herein, the term "extraction" refers to any process or technique which is applied prior to alkaline treatment with the intent of removing soluble components from the lignocellulosic material. Whilst such extraction will generally be applied to remove non-fermentable, soluble components contained in the lignocellulosic material, such as proteins, amino acids and soluble inorganic components, it is also envisaged that pre-extraction may be employed to remove soluble, fermentable components from the biomass.

In several embodiments, a pre-treatment may comprise a physicochemical treatment. In particular a physicochemical treatment may preferably comprise a steam treatment. A steam treatment may generally result in the auto-hydrolysis of the lignocellulosic material.

A pretreatment may preferably comprise at least one of an acid treatment (acid hydrolysis), a solvent treatment (extraction), and a steam treatment A combination of several treatments may be performed. For instance, a pretreatment may comprise a physical treatment in combination with a chemical treatment. For instance a pre-treatment may comprise comminuting a lignocellulosic material and subjecting the comminuted lignocellulosic material to an acid treatment or a steam treatment.

Typically during a pre-treatment (such as a steam treatment or acid treatment) the pH of the lignocellulosic material may be reduced. The reduction of the pH may be due to the addition of acid as such (e.g. in an acid treatment) but also due to the liberation of acids during the hydrolysis of the lignocellulosic material which typically takes place during a pre-treatment (e.g. in a steam treatment). In several embodiments prior to the alkaline treatment as described herein the pH of the lignocellulosic material may be, e.g., from 1 to 7, in particular from 1.5 to 6, and more in particular from 2 to 4.

An alkaline treatment with a magnesium-containing alkaline agent as described herein may be performed in addition to or alternatively to a pre-treatment as defined above. The alkaline treatment may also be performed simultaneously to other treatments. Particular examples include, e.g., using an alkaline agent comprising a caustic magnesium salt in combination with oxidizing agent (such as $H_2O_2$) and using an alkaline agent comprising a caustic magnesium salt during extrusion.

An alkaline treatment as described herein may be performed to break down the lignocellulosic material as described above for the pre-treatments or, in the case where a pre-treatment has been effected prior to the treatment with a caustic magnesium salt, to further break down the pre-treated lignocellulosic material. Any of the conditions indicated above for the alkaline treatment may be used. In particular, such a treatment may be performed with reaction mixture has a concentration of caustic magnesium salt of from 5 to 25% (w/w) and/or at pH from 9.0 to 12.0, in combination with a temperature of: either I) from 170° to 200° C. for a period of from 1 to 240 minutes, preferably from 1 to 120 minutes; or, ii) from 140° to 170° C. for a period of from 180 to 600 minutes, preferably from 240 to 480 minutes.

Alternatively or additionally, an alkaline treatment as described herein may be performed to adjust the pH of a lignocellulosic material to a pH which is suitable for, e.g., a subsequent saccharification by enzymatic hydrolysis. This may be the case, for instance, when a lignocellulosic material is subjected to an acid pre-treatment or a pre-treatment resulting in the liberation of acid (e.g. as described above) and is then neutralised by treatment with an alkaline agent comprising a caustic magnesium salt. Any of the conditions indicated above for the alkaline treatment may be used. In particular, such neutralization may be performed at a pH from 2.0 to 10.0, typically from 4.0 to 9.0, more in particular from 4.5 to 8.0, and yet more in particular from 4.5 to 5.5, optionally a temperature from 15 to 100° C., preferably from 30 to 80° C. and optionally for a time period from less than 1 minute to 30 minutes, in particular from 1 minute to 15 minutes.

An alkaline treated lignocellulosic material as described herein may be subjected to additional treatments prior to a subsequent saccharification similar to those described above as pre-treatments and other suitable treatments which may be known in the art.

For instance, the alkaline treated lignocellulosic material may be subjected to an acid treatment. An acid treatment may be performed to, e.g., adjust the pH to a pH suitable for a subsequent saccharification by enzymatic hydrolysis in those cases where the pH of the alkaline treated lignocellulosic material is outside a suitable range. For instance, the pH may be adjusted to from 2.0 to 10.0, in particular 4.0 to 9.0, more in particular from 4.5 to 8.0, and yet more in particular from 4.5 to 5.5. An acid treatment may be preferably performed with lactic acid. The use of lactic acid is particularly advantageous in a method as described herein wherein the alkaline treated lignocellulosic material is to be used for providing lactic acid as it advantageously precludes the need for the acid to be removed at a later stage.

Additionally or alternatively, the alkaline treated lignocellulosic material may be subjected to a solid/liquid separation, using known methods such as centrifugation and/or filtration (e.g., microfiltration, plate and frame filtration, cross-flow filtration, pressure filtration, vacuum filtration and the like).

Additionally or alternatively, the alkaline treated lignocellulosic material may be washed. For instance, the alkaline treated lignocellulosic material may be treated with a solvent, e.g., to perform an extraction to remove non-fermentable soluble components such as solubilized lignin, proteins, amino acids or soluble inorganic components (e.g., metal ions) contained in the lignocellulosic material which may interfere with a subsequent saccharification and/or fermentation. The treated lignocellulosic material may also be washed with an aqueous solution to produce a wash stream, and a solids stream comprising the treated lignocellulosic material.

As described in detail above a method as described herein comprises a treatment with an alkaline agent comprising a caustic magnesium salt alone or in combination with other treatments.

In several specific embodiments a method as described herein may comprise prior to saccharification:

a physicochemical treatment comprising mechanical comminuting and steam treatment (e.g. steam explosion) followed by a treatment with alkaline agent comprising a caustic magnesium salt;

a physical treatment such as mechanical milling, extrusion, preferably mechanical milling, followed by a treatment with alkaline agent comprising a caustic magnesium salt;

an acidic treatment (e.g. mild acid treatment or a sulphite treatment) followed by a treatment with alkaline agent comprising a caustic magnesium salt, optionally comprising lignin extraction;

a neutral treatment (e.g. a physical treatment as described above such as steam explosion, without addition of acid) followed by a treatment with alkaline agent comprising a caustic magnesium salt;

a treatment with an alkaline agent comprising a caustic magnesium salt followed by an acidic treatment (e.g. neutralization with lactic acid);

a treatment with alkaline agent comprising a caustic magnesium salt followed by a neutral treatment such as a steam explosion treatment, optionally comprising alkaline extraction of acetyl groups;

a physical treatment such as extrusion or refining in the presence of an alkaline agent comprising a caustic magnesium salt.

A lignocellulosic material treated with a magnesium-containing alkaline agent as described herein, may be advantageously used in the production of lactic acid and/or lactate salt by separate saccharification and fermentation wherein a magnesium-containing alkaline agent is used for neutralization during fermentation. The use of a magnesium-containing alkaline agent in such a method precludes the need for its removal between saccharification and subsequent fermentation. The use of an alkaline agent comprising a caustic magnesium salt and subsequent separate saccharification and fermentation (with a caustic magnesium salt as a neutralizing agent) also facilitates downstream processing of a method for the preparation of lactic acid and/or lactate salt, as explained in detail below. Further, in such a method any caustic magnesium salt separated during, e.g., recovery of lactic acid and/or lactate salt, may be recycled to an alkaline treatment step as described herein, minimizing waste products.

Generally, the lignocellulosic material treated with a magnesium-containing alkaline agent as described herein may be subjected to separate saccharification and fermentation, wherein the saccharification and/or the fermentation are performed at a pH from 2.0 to 10.0, in particular from 4.0 to 9.0; and optionally at a temperature from 30 to 80° C., in particular from 45 to 70° C.

A method as described herein comprises saccharifying an alkaline treated aqueous lignocellulosic material as described herein to provide a saccharified aqueous lignocellulosic material, herein also referred to as saccharified lignocellulosic material.

In the context of the process as described herein, the term saccharification refers to the hydrolysis of polysaccharides into fermentable carbohydrates, which may be used as substrates in a subsequent fermentation step. Saccharification is preferably performed by enzymatic hydrolysis. Even though hydrolysis may occur during an alkaline treatment as described herein or during a pre-treatment step, the bulk of hydrolysis of the polymeric carbohydrates in the lignocellulosic material takes place during saccharification.

Saccharification may be performed continuously, in batch mode or in fed-batch mode.

Saccharifying a treated lignocellulosic material may be performed by incubating the treated lignocellulosic material with a hydrolytic enzyme at a suitable temperature and pH, for a suitable time period.

Any suitable hydrolytic enzyme known in the art for the hydrolysis of polysaccharides into fermentable carbohydrates may be used. Mixtures of hydrolytic enzymes may also be used. A hydrolytic enzyme preferably is at least one of cellulase and hemicellulase, also referred to as cellulolytic or hemicellulolytic enzymes, and more preferably is a cellulase. Cellulases such as CBH1, CBH2, EG, and BGL; GH61 polypeptides having cellulolytic enhancing activity as described in, for example WO2005/074647, WO 2008/148131, and WO 2011/035027, may be particularly preferred. Other hydrolytic enzymes that may be used include, e.g., expansins; esterases, such as acetylxylan esterase (EC 3.1.1.72) that catalyzes the hydrolysis of acetyl groups from polymeric xylan, acetylated xylose, acetylated glucose, alpha-napthyl acetate, and p-nitrophenyl acetate; laccases; ligninolytic enzymes; pectinases; peroxidases; proteases; amylolytic accessory enzymes; inulinases, levanases; and swollenins.

Depending on the temperature of the alkaline treated lignocellulosic material and on the temperature used in a subsequent saccharification step the treated lignocellulosic material may be heated or cooled prior to saccharification.

Depending on the pH of the alkaline treated lignocellulosic material and the pH for a subsequent saccharification step, the pH of the treated lignocellulosic material may be adjusted prior to saccharification. For instance, the pH may be adjusted by adding additional alkaline agent comprising a caustic magnesium salt or adding a caustic salt other than a caustic magnesium salt (such as NaOH, $Na_2CO_3$, $NaHCO_3$, KOH, $K_2CO_3$, $KHCO_3$, CaO, $Ca(OH)_2$, $CaCO_3$, $Ca(HCO_3)_2$, $NH_4OH$, $(NH_4)_2CO_3$, and $NH_4HCO_3$, preferably NaOH and/or KOH) to the treated lignocellulosic material to increase its pH. The pH may also be adjusted by adding an acid to the treated lignocellulosic material to decrease its pH (e.g. lactic acid, hydrochloric acid, sulfuric acid and/or nitric acid, preferably lactic acid or hydrochloric acid, more preferably lactic acid). PH adjustment prior to saccharification may be typically performed by acidification.

The conditions of saccharification may depend on the hydrolytic enzyme used.

Saccharification may be performed, e.g., at a temperature from 30 to 80° C., in particular from 45 to 70 ° C. More in particular saccharification may be performed at a temperature from 50 to 60° C. or even more in particular from 50 to 55° C.

Saccharification may be performed, e.g., at a pH from 2.0 to 10.0, and is generally performed at a pH from 4.0 to 9.0, in particular from 4.5 to 8.0. More in particular saccharification may be performed at a pH from 4.5 to 5.5.

In several embodiments saccharification may be performed at a temperature form 50 to 60° C. and a pH from 4.5 to 5.5.

Saccharification may be performed until a suitable degree of hydrolysis is obtained. For instance, the degree of hydrolysis may be from 20% to 99%, in particular from 50% to 95%%. Preferably the degree of hydrolysis may be of at least 80%, even more preferably of at least 90%. A degree of hydrolysis of 100% may also be achieved. The degree of hydrolysis may be calculated based on the amount of glucose measured divided by the theoretical maximum amount of glucose. The amount of glucose may be measured by methods known in the art, for example by HPLC or enzymatic reaction, and the theoretical maximum amount of glucose is based on the original content of cellulose in the treated lignocellulosic material.

Generally, saccharification may be performed for a period of time from 1 hour to 2 weeks, in particular from 12 hours to 1 week, more in particular about 72 hours. The specific time may depend on the conditions of choice and the degree of conversion desired. For a saccharification mixture comprising 15 wt. % of dry lignocellulosic material a conversion of at least 80 wt. % may be typically obtained after running the saccharification for about 72 h.

A saccharified aqueous lignocellulosic material as described herein generally comprises fermentable carbohydrates and a solid lignocellulosic fraction. Fermentable carbohydrates generally are in solution and the solid lignocellulosic fraction generally is in suspension.

The solid lignocellulosic fraction generally comprises unhydrolyzed cellulose, unhydrolyzed hemicellulose and undissolved lignin.

Prior to a subsequent fermentation, the saccharified lignocellulosic material may be subjected to a separation step to separate the solid lignocellulosic fraction from the fermentable carbohydrates in the saccharified lignocellulosic material. Part or substantially all of the solid lignocellulosic fraction may be removed. The separation step preferably provides a saccharified lignocellulosic material comprising fermentable carbohydrates and being substantially free from solid lignocellulosic fraction. Preferably the saccharified lignocellulosic material is free of solid lignocellulosic fraction and any other solid/insoluble particles. Substantially free as used herein means that the saccharified aqueous lignocellulosic material comprises at most 5 wt. % of solid lignocellulosic fraction, based on the dry weight of solid lignocellulosic fraction and total weight of saccharified aqueous lignocellulosic material. In particular, a saccharified lignocellulosic material substantially free of solid lignocellulosic fraction may comprise at most 1 wt. %, more in particular at most 0.5 wt% and yet more in particular at most 0.1 wt. % of solid lignocellulosic fraction.

A separation step used to remove solid lignocellulosic fraction may generally be a solid / liquid separation and may be performed by methods known in the art. In particular, by filtration (e.g. pressure filtration or vacuum filtration), centrifugation, flotation, sedimentation, decantation, and flocculation.

The separated solid lignocellulosic fraction may be recycled. For instance, the solid lignocellulosic fraction may be incorporated to an up stream (e.g. alkaline) treatment step, in particular to an alkaline treatment as described herein. By doing so the yield of fermentable carbohydrates obtained from a lignocellulosic material may be advantageously increased. Recycling may require a purging step.

Removal of solid lignocellulosic fraction at this stage advantageously facilitates subsequent fermentation and recovery steps, and ultimately may result in improved overall yields and improved purity of the lactic acid and/or lactate salt product. In particular, removal of the solid lignocellulosic fraction advantageously reduces the viscosity of the saccharified lignocellulosic material which facilitates and favours a subsequent fermentation. In particular a process as described herein requires less energy for mixing and less issues in fermentation as no slurries are being handled. Removing the solid lignocellulosic fraction at this stage also reduces the volume that needs to be processed, providing an improved method of preparation, e.g., which is easier to perform and which is more cost effective. Without being bound to any theory, it is also contended that the presence of the solid lignocellulosic fraction during fermentation may negatively interact with the microorganisms used for fermentation.

Additionally or alternatively, the saccharified lignocellulosic material may be subjected to treatments other than a solid/liquid separation as described herein. Preferably such treatments may be performed after said solid /liquid separation.

In several embodiments a process as described herein comprises subjecting the saccharified aqueous lignocellulosic material to a concentration step prior to the fermentation step. Concentration may be generally performed to increase the concentration fermentable carbohydrates in the saccharified aqueous lignocellulosic material. Preferably concentration may be performed after removal of the solid lignocellulosic fraction by solid / liquid separation. Concentration may be performed by, e.g., evaporation of water. For instance the amount of fermentable carbohydrates in the saccharified lignocellulosic material may be increased to favour fermentation. For instance the concentration of fermentable carbohydrates achieved after concentration may be that specified below for the fermentation medium.

Additional treatments that may be performed prior to fermentation, preferably after removal of the solid lignocellulosic fraction, include, e.g., carbon treatment, ion exchange, membrane treatment, extraction. Such treatments may be performed to, e.g., eliminate impurities. Some of the impurities that may be eliminated include compounds which may act as inhibitors of lactic acid producing microorganisms used during the fermentation, such inhibitors may include, for instance, furfural, 5-hydroxymethylfurfural (5-HMF), phenolics and acetic acid. Accordingly, in several embodiments a process as described herein comprises subjecting the saccharified aqueous lignocellulosic material to a detoxification step prior to the fermentation step.

A process as described herein comprises fermenting fermentable carbohydrates in the saccharified aqueous lignocellulosic material by means of a lactic acid producing microorganism in the presence of an alkaline agent comprising a caustic magnesium salt to provide an aqueous fermentation broth comprising magnesium salt of lactic acid.

Fermentation may be performed continuously, in batch mode or fed-batch mode.

Fermentation is generally performed by providing a fermentation medium comprising fermentable carbohydrates of a saccharified aqueous lignocellulosic material as described herein. The fermentation medium may be a saccharified aqueous lignocellulosic material as such (which may comprise solid lignocellulosic fraction or may be (substantially) free of solid lignocellulosic fraction). Alternatively, the fermentation medium may be provided by mixing the saccharified aqueous lignocellulosic material (with or without solid lignocellulosic fraction) with water and/or additional nutrients.

In another embodiment, the fermentation medium comprises additional nutrients besides the saccharified lignocellulosic material. The fermentation medium may be provided by mixing the additional nutrients with saccharified lignocellulosic material and, optionally, water. The additional nutrients may be added in any order and in solid form, in solution (e.g. in water) or in suspension (e.g. in water).

Additional nutrients may be selected from at least one of, for instance, mineral salts (e.g. a source of mineral nitrogen, phosphate, sulfur and trace elements such as zinc, magnesium, calcium, manganese, potassium, sodium, boric, iron, cobalt, copper, molybdenum, nickel, aluminum, etc.), a carbohydrate source other than the fermentable carbohydrates of the saccharified lignocellulosic material (e.g. glucose, maltose, fructose, xylose, sucrose, etc.) and a source of organic nitrogen (e.g. yeast autolysates and hydrolysates, plant protein hydrolysates, animal protein hydrolysates, soluble by-products from steeping wheat or maize, etc.). Such organic nitrogen sources generally provide nitrogen in the form of, e.g., free amino acids, oligopeptides, peptides, vitamins and traces of enzyme cofactors. Even though the additional nutrients may include carbohydrate sources, it is preferred that the saccharified lignocellulosic material is the only carbohydrate source. This simplifies the process and avoids the use of expensive carbohydrate sources.

The addition of sugars to the fermentor may be performed continuously, in batch mode or fed-batch mode. The total amount of fermentable carbohydrates in the fermentor (including lignocellulosic derived carbohydrates as well as added sugars) at the begin of the fermentation may be from 5 to 60 wt. %, based on the total weight of fermentation medium prior to inoculation with a lactic acid producing microorganism. In several embodiments the amount of fermentable carbohydrates may be from 10 to 50 wt. %, more in particular from 15 to 30 wt. %. In several embodiments the amount of fermentable carbohydrates may be from 20 to 60 wt. %, in particular from 30 to 50 wt. %, e.g. after concentrating the saccharified lignocellulosic material. The content of fermentable carbohydrates may be determined by methods known in the art. Particularly instructive disclosures are: Milne et al., Sourcebook of Methods of Analysis for Biomass Conversion and Biomass Conversion Processes. SERI/SP-220-3548. Golden, CO: Solar Energy Research Institute, February 1990; and National Renewable Energy Authority Determination of Structural Carbohydrates and Lignin in Biomass: Laboratory Analytical Procedure (LAP), Revised August 2012, http://www,nrel.gov/docs/gen/fy13/42618.pdf. For instance, the amount of fermentable carbohydrates may be measured by high-pH anion exchange chromatography. A sample of the fermentation medium is filtered to separate the liquid phase from any solid particles and a chromatogram of the liquid phase is obtained, e.g. with a pulsed amperometric detector (HPAEC-PAD). The carbohydrate composition of the liquid phase may then be determined based on a calibration performed by using appropriate standards (e.g. C5, C6 and/or C12 sugar standards).

Fermentation may be performed by methods known in the art. Generally, a lactic acid producing microorganism is added to the fermentation medium. The microorganism-containing fermentation medium is then mixed by, e.g., agitating and/or stirring.

The pH of the fermentation medium may be adjusted to a pH suitable for fermentation with the microorganism of choice and this may be done prior to addition of the microorganism, if the pH of the saccharified lignocellulosic material is outside a suitable range. Generally, the pH may be adjusted to a pH from 2.0 to 10.0, in particular from 4.0 to 9.0, more in particular from 4.5 to 8.0. Yet more in particular the pH may be adjusted to a pH from 5.5 to 7.5. For instance, neutral pH fermentation may be performed at a pH from 6.0 to 8.0. Low pH fermentation may be performed at a pH from 2.0 to 4.5. Adjusting the pH may be performed as described above for the treated lignocellulosic material. Depending on the initial pH of the fermentation medium, adjusting the pH may be performed by addition of a base (e.g. an alkaline agent comprising a caustic magnesium salt) or an acid (e.g. lactic acid and/or hydrochloric acid, preferably lactic acid) to said saccharified lignocellulosic material.

The fermentation medium is fermented by means of a lactic acid producing microorganism in the presence of an alkaline agent comprising a caustic magnesium salt to provide a fermentation broth containing magnesium salt of lactic acid. The fermentation is generally performed by incubating the fermentation medium with the microorganism at a suitable temperature for a suitable period of time.

Suitable lactic acid producing microorganisms may include bacteria, fungi and yeasts.

Lactic acid producing microorganisms may be selected from species that are (a) homolactic lactic acid producers, (b) heterofermentative species which produce lactic acid or (c) species that are genetically modified to produce lactic acid. Examples of such species include but are not limited to species of bacteria such as *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, Weissella, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*), *Caldicellulosiruptor* (including *Caldicellulosiruptor saccharolyticus*), *Clostridium* (including *Clostridium thermocellum*), *Thermoanaerobacterium* (including *Thermoanaerobacterium saccharolyticum*), *Thermoanaerobacter* and *Escherichia* (including *Escherichia coli*) and species of fungi and yeast such as *Saccharomyces* (including *Saccharomyes cerevisiae*), *Kluyveromyces* (including *Kluyveromyces lactis* and *Kluyveromyces marxianus*), *Issatchenkia* (including *Issatchenkia orientalis*), *Pichia* (including *Pichia stipitis*), *Candida* (including *Candida boidinii, Candida magnolia, Candida methanosorbosa, Candida sonorensis* and *Candida utilis*) and *Rhizopus* (including *Rhizopus arrhizus, Rhizopus microspores* and *Rhizopus oryzae*).

Bacterial genera that may be of particular interest are *Lactobacillus, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*) and *Escherichia* (including *Escherichia coli*). Additionally or alternatively, preferred bacterial species are those that display optimal growth at a pH in the range of about 5 to about 8.

The incubation temperature may depend on the microorganism used. It is within the scope of a person skilled in the art to choose a suitable temperature. For example, the optimum temperature to be used may be established by analyzing the activity of the fermentation microorganism under different temperature conditions. Generally, the temperature may be from 30 to about 80° C., in particular from 45 to 70° C. More in particular fermentation may be performed at a temperature from 50 to 60° C.

An alkaline agent comprising a caustic magnesium salt is generally added to the fermentation medium to neutralize the lactic acid excreted by the microorganisms during fermentation generating a magnesium lactate salt. A drop in pH below a critical value, depending on the microorganism used in the process, could damage the metabolic process of the microorganism and bring the fermentation process to a stop. The pH is generally adjusted during fermentation to be from 4.0 to 9.0, in particular from 4.5 to 8. More in particular the pH may be adjusted during fermentation from 5.5 to 7.5. In one embodiment fermentation may be performed at a temperature from 50 to 60° C. and at a pH from 5.5 to 7.5.

Adjusting the pH during fermentation may be performed by controlling the pH of the fermentation medium and by addition of appropriate amounts of base when necessary. A caustic magnesium salt of the alkaline agent as described herein may be selected from at least one of MgO, $Mg(OH)_2$, $MgCO_3$ and $Mg(HCO_3)_2$, alkaline magnesium silicate, tri-magnesium phosphate, and mono-magnesium phosphate. Preferably, the caustic magnesium salt is selected from at least one of MgO, $Mg(OH)_2$, $MgCO_3$, and $Mg(HCO_3)_2$. More preferably, the caustic magnesium salt comprises MgO and/or $Mg(OH)_2$. The alkaline agent may comprise a base other than a caustic magnesium salt such as a caustic such as ammonia, a caustic sodium salt, a caustic potassium salt, caustic calcium salt and/or a caustic ammonium salt, such as NaOH, $Na_2CO_3$, $NaHCO_3$, KOH, $K_2CO_3$, $KHCO_3$, CaO, $Ca(OH)_2$, $CaCO_3$, $Ca(HCO_3)_2$, $NH_4OH$, $(NH_4)_2CO_3$, and $(NH_4)HCO_3$. Ammonia may be also be used as additional base. The use of a caustic magnesium salt without said other bases may be preferred. In particular, the alkaline agent may comprise predominantly a magnesium salt (e.g. more than 90 wt. %, 95 wt. %, preferably more than 98 wt. %, based on the total weight amount of alkaline agent) or even consist of solely a caustic magnesium salt. Accordingly, the alkaline agent may comprise or consist of at least one of MgO, $Mg(OH)_2$, $MgCO_3$ and $Mg(HCO_3)_2$. The alkaline agent may preferably comprise or even consist of MgO and /or $Mg(OH)_2$.

The total amount of caustic magnesium salt to be added in a process as described herein may be determined by the molar amount of magnesium ion and the molar amount of lactic acid to be neutralized to form a magnesium salt of lactic acid. For instance, the total amount of caustic magnesium salt (including any caustic magnesium salt present in the saccharified lignocellulosic material derived from the alkaline treatment with a magnesium-alkaline agent) may be ½ mol of caustic magnesium salt selected from at least one of MgO, $Mg(OH)_2$, $MgCO_3$, and $Mg(HCO_3)_2$ per 1 mol of lactic acid. Generally, the total amount of caustic magnesium salt may be from 5 to 40 wt. % of caustic magnesium salts based on the total weight of dry lignocellulosic material subjected to magnesium-alkaline treatment, in particular from 10 to 35 wt. %.

Generally, the fermentation may preferably be stopped when the fermentation broth is substantially free of fermentable carbohydrates, e.g. when the content of fermentable carbohydrates in the liquid phase of the fermentation broth is below 5 g/l. The amount of fermentable carbohydrates may be monitored by subjecting samples of the fermentation broth to a solid/liquid separation step, to remove any solids from the liquid phase, and measuring the content of C5, C6 and/or C12 sugars in the liquid phase as described earlier for the fermentation medium.

In a process as described herein saccharification step and fermentation are performed as two separate steps. Such processes are known in the art as separate hydrolysis and fermentation (SHF). In the context of this application, a separate saccharification and fermentation, means that saccharification is performed in the absence of lactic acid producing microorganisms, in other words no lactic acid producing microorganism is actively added to the lignocellulosic material during saccharification. However, in a process as described herein, saccharification may occur in the presence of small amounts of lactic acid producing microorganisms, that may be present due to contamination, e.g., from the environment. The amount of lactic acid resulting from the presence of lactic producing mircoorganisms in the saccharification, is generally below 10 wt. %, in particular below 5 wt. %, and more in particular below 0.1 wt. %, based on the total weight amount of saccharified lignocellulosic material.

Saccharification and fermentation may be performed in a single reactor by, e.g., adding lactic acid producing microorganisms to the saccharified lignocellulosic material once a desired degree of saccharification has been achieved, e.g., a degree of saccharification as indicated above.

Saccharification and fermentation may be performed in several reactors, at least two reactors, connected in series. Saccharification may take place in a first reactor comprising hydrolytic enzymes (without lactic acid producing microorganisms), and fermentation may take place in a second reactor comprising lactic acid producing microorganisms.

A separate saccharification and fermentation allows for the removal of solid lignocellulosic fractions present in the saccharified lignocellulosic material prior to fermentation as described above. The removal of the solid lignocellulosic fraction advantageously improves the fermentation and subsequent method steps. In particular, by removal of solid lignocellulosic fraction the viscosity of the saccharified lignocellulosic material may be reduced, a higher yield of lactic acid production may be achieved or a target yield of lactic acid may be achieved in a shorter time period. Further, the processing of the fermentation broth is facilitated.

Further, by having a separate saccharification and fermentation, each step can be operated at different pH and temperature, hence operating at the optimum conditions for each process steps. The optimum conditions for each step will depend on the hydrolytic enzyme and microorganism of choice for saccharification and fermentation respectively. Other factors, such as the nature of the lignocellulosic material used or the caustic magnesium salt used in the alkaline treatment may also influence optimal conditions. Optimal conditions for saccharification may be, e.g., a pH from 4.5 to 5.5 and a temperature from 50 to 60° C. Optimal conditions for fermentation may be, e.g., a pH from 5.5 to 7.5, and a temperature from 50 to 60° C.

Furthermore, as described above, a separate saccharification and fermentation improves the removal of impurities, e.g. solid lignocellulosic fraction, and/or inhibitors, which may adversely affect fermentation, e.g by reducing the activity of the microorganisms used during fermentation.

An aqueous fermentation broth provided by a fermentation as described herein comprises magnesium lactate. In one embodiment, the fermentation broth comprises magnesium lactate in solution. In another embodiment, the fermentation broth comprises magnesium lactate in solid form. Magnesium lactate in solid form may comprise magnesium lactate crystals. Preferably, the fermentation broth comprises magnesium lactate crystals. It is understood that in case of a fermentation broth comprising magnesium lactate in solid form, the fermentation broth also comprises magnesium lactate in solution, i.e. a saturated solution of magnesium lactate.

An aqueous fermentation broth provided by a fermentation as described herein comprises a microorganism fraction comprising lactic acid producing microorganisms used in the fermentation.

The aqueous fermentation broth may further comprise other solid impurities, such as impurities derived from the fermentation and/or derived from the lignocellulosic material (e.g. a solid lignocellulosic fraction as described above).

If a separation step has been performed prior to fermentation to remove solid lignocellulosic fraction from the saccharified lignocellulosic material, the fermentation broth may generally be substantially free of solid lignocellulosic fraction. Preferably the aqueous fermentation broth is free of solid lignocellulosic fraction. Substantially free as used herein means that the aqueous fermentation broth comprises at most 5 wt. % of solid lignocellulosic fraction, based on the total weight of fermentation broth including the microorganism fraction. In particular, a fermentation broth substantially free of solid lignocellulosic fraction may comprise at most 1 wt. %, more in particular at most 0.5 wt. % and yet more in particular at most 0.1 wt. % of solid lignocellulosic fraction.

A process as described herein comprises isolating lactic acid and/or lactate salt from an aqueous fermentation broth comprising magnesium lactate as described above. Isolation of the lactic acid and/or lactate salt may also be referred to as recovery. In this step the targeted fermentation product (lactic acid in the form of magnesium lactate) is isolated or recovered from the fermentation broth. Isolating may comprise at least one of a separation (e.g. solid/liquid separation), a concentration, cooling step, a crystallisation (e.g. evaporation crystallisation and/or cooling crystallisation) and a washing step. The isolation preferably comprises a separation and, optionally, a crystallization. A solid/liquid separation may be preferred. A solid/liquid separation may comprise, for example, flotation, sedimentation, flocculation, centrifugation, filtration and combinations thereof. Filtration may comprise at least one of microfiltration, plate and frame filtration, crossflow filtration, pressure filtration, and vacuum filtration. Crystallization may comprise a concentration and/or cooling step. Concentration may be performed by removal of water (e.g. under vacuum). Part of this concentration step may already take place during the fermentation. Concentration may optionally be followed by cooling. Concentration and/or cooling may provide magnesium lactate in solid form, in particular magnesium organic salt crystals, resulting in a crystallisation. Cooling may be performed to reach temperatures below 20° C. However, it is generally preferred for the crystallization to take place a temperature from 20 to 95° C., in particular from 50 to 90° C. Crystallization at these temperatures (e.g. without cooling) may advantageously allow a higher amount of other impurities, to remain in the liquid phase, thereby avoiding their co-precipitation or co-crystallization with the magnesium lactate crystals.

In several embodiments, an isolation as described herein comprises subjecting a fermentation broth comprising magnesium lactate in solution to a solid/liquid separation to provide a separated liquid phase comprising magnesium lactate in solution and a separated solid phase comprising a solid residue. The solid/liquid separation may be preferably performed at a temperature from 20 to 75° C., in particular from 25 to 70° C., and more in particular from 30 to 60° C. Advantageously, at these temperatures are high enough for the magnesium lactate to remain in solution whilst maintaining some other components in the solid state. By performing the solid/liquid separation at these temperatures the separation may be improved. At said temperatures the viscosity of the filtrate may also be lower. Optionally, the separated liquid phase comprising magnesium lactate in solution may be subjected to concentrating and/or cooling, providing a separated liquid phase comprising magnesium lactate in solid form, preferably comprising magnesium lactate crystals. The so obtained liquid phase comprising magnesium lactate in solid form may be subjected to a second solid/liquid separation to provide separated solid magnesium lactate, preferably comprising magnesium lactate crystals.

In several embodiments an isolation as described herein comprises subjecting a fermentation broth comprising magnesium lactate in solution to concentration and/or cooling to provide a fermentation broth comprising magnesium lactate in solid form and subjecting the fermentation broth comprising magnesium lactate in solid form to a solid/liquid separation to provide a separated solid phase comprising magnesium lactate in solid form. The magnesium lactate in solid form preferably comprises magnesium lactate crystals. The separation will also provide a separated liquid phase. The separated liquid phase may comprise a solid residue (e.g. in suspension).

In several embodiments an isolation as described herein comprises subjecting a fermentation broth comprising magnesium lactate in solid form to a solid/liquid separation to provide a separated solid phase comprising magnesium lactate in solid form. The separated solid magnesium lactate may preferably comprise magnesium lactate crystals. The separation will also provide a separated liquid phase. The separated liquid phase may comprise a solid residue (e.g. in suspension).

A solid/liquid separation to separate magnesium lactate in solid form (e.g. magnesium lactate crystals) may be performed by, e.g., filtration using a filter with a suitable pore size to retain solid magnesium lactate (e.g. magnesium lactate crystals) on the filter and to enable subsequent removal of impurities including any remaining solid residue by, e.g., washing of the filter cake. The solid/liquid separation may also be performed taking advantage of the difference in density between the solid magnesium lactate and the solid residue. For instance a cyclone separator may be used. Cyclone separators are known in the art. Reference is made to for instance U.S. Pat. No. 4,734,109, which contents are incorporated herein by reference.

The solid residue in the separated liquid or solid phases generally comprises a microorganism fraction (also referred to in the art as biomass) and, optionally, a solid lignocellulosic fraction. The solid residue may comprise other solid impurities, such as impurities derived from the fermentation. If the solid lignocellulosic fraction is removed from the saccharified lignocellulosic material prior to fermentation, the separated solid residue may generally be substantially free of solid lignocellulosic fraction. Preferably the separated solid residue is free of solid lignocellulosic fraction. Substantially free as used herein means that the solid residue comprises at most 5 wt. %, preferably at most 1 wt. %, more preferably at most 0.5 wt. %, yet more in particular at most 0.1 wt. % of solid lignocellulosic fraction. The wt. % is based on the total mass of solid residue.

A fermentation broth comprising magnesium lactate in solid form (e.g. comprising magnesium lactate crystals) advantageously allows easy separation of magnesium lactate from other impurities present in the fermentation broth in particular impurities originating from the lignocellulosic material (e.g. solid lignocellulosic fraction) as well as any impurities derived from the fermentation (e.g. microorganism fraction). The separated impurities may be sent to waste water or may advantageously be used to produce biogas or for energy recovery.

A fermentation broth comprising magnesium lactate in solution advantageously allows for a control of the crystallization of magnesium lactate, allowing for a flexibility in performing a solid/liquid separation prior to and/or after crystallization as described above. This control and flexibility advantageously allows improving the removal of the solid and soluble impurities present in the fermentation broth. These impurities may be converted, e.g., after separation from the magnesium lactate, into a fertilizer or used directly as a fertilizer. Conversion of the impurities into a fertilizer may comprise at least one processing step selected from an evaporation, a concentration, a chemical reaction (e.g. with phosphates, ammonia and/or potassium salts), a precipitation and a solid/liquid separation. Examples of fertilizers that may be obtained include fertilizers rich in magnesium (e.g. struvite).

A process described herein preferably comprises a solid/liquid separation step to provide a separated solid phase comprising magnesium lactate in solid form and a separated liquid phase. As indicated above the separated liquid phase may comprise a solid residue (e.g. in suspension).

A separated liquid phase may be optionally recycled to a previous step in the process as described herein, e.g., to the saccharification step. Such recycling step may advantageously reduce the amount of fresh water needed to be added to the system. Further, such a recycling step may reduce losses of residual magnesium lactate present in the liquid phase. Preferably any solid residue that may be present in the separated liquid phase may be removed prior to recycling (e.g. by an additional solid/liquid separation).

Generally, the yield of recovery of lactic acid in the form of magnesium lactate, e.g., in the form of magnesium lactate crystals, may be from 50% to 99%, in particular from 70% to 95% based on the amount of lactic acid produced during fermentation.

A process as described herein advantageously provides a magnesium lactate, and any lactate salt or lactic acid derived therefrom of high purity, despite of using lignocellulosic material as carbohydrate source. For instance, a magnesium lactate separated by a method as described herein (e.g. comprising magnesium lactate crystals) may have a purity of 90 to 99.9 wt. %, in particular from 95 to 99.5 wt. %, more in particular from 98 to 99 wt. %.

Magnesium lactate obtained by fermentation may be further processed to further increase the purity of the magnesium lactate, to provide other lactate salts and/or to provide lactic acid.

Further processing steps may be performed directly on the fermentation broth comprising magnesium lactate (in solution or in solid form, e.g. comprising magnesium lactate crystals). By performing further processing steps directly on the fermentation broth comprising magnesium lactate, a process to obtain a lactate salt or lactic acid may be advantageously shortened, may be less costly and the lactate salt/lactic acid recovery yields may be improved by avoiding one or more of the separation steps described above.

Further processing steps may be performed after a separation as described above, i.e. on a separated phase comprising magnesium lactate, preferably comprising magnesium lactate in solid form, and more preferably comprising magnesium lactate crystals. By performing further processing steps on a separated phase comprising magnesium lactate as described herein the magnesium lactate may be transformed into lactic acid or into a different lactate salt.

Additionally, or alternatively, further processing steps may be performed to improve the purity of the magnesium lactate and any lactate salt or lactic acid obtained therefrom.

In several embodiments, the magnesium lactate may be treated with an acid (e.g. hydrochloric acid, sulfuric acid and/or nitric acid, preferably hydrochloric acid) in the presence of water to provide lactic acid in solution and an insoluble magnesium salt. For instance, if hydrochloric acid is the acid used, magnesium chloride is obtained. The lactic acid may then be separated from the magnesium salt by, e.g., a liquid/liquid separation, e.g. including extraction and back extraction steps (reference is made to, e.g., WO/2013/093047 the content of which is incorporated herein by reference). The magnesium salt, and magnesium chloride in particular, may advantageously be subjected to a thermal salt splitting (TSS) process to provide magnesium oxide and hydrochloric acid. TSS may be performed, for instance, as described in WO0017378, WO 2013/025107, WO 2013/093028, and WO 2013/093047 and WO 2013/174911, of which the contents are incorporated herein by reference. The use of TSS advantageously allows for the so obtained magnesium oxide and/or hydrochloric acid to be recycled into the process as described herein. A small fraction of the lactic acid obtained may also be recycled back into the production process, e.g., in the acidulation of the alkaline treated lignocellulosic biomass prior to hydrolysis as described above.

In an interesting embodiment of the presently recited method, step d) comprises recovering magnesium lactate from said aqueous fermentation broth, and said method further comprises: e) providing a feed comprising hydrogen chloride, said feed being either an aqueous solution comprising hydrogen chloride or a gas feed comprising gaseous hydrogen chloride; f) acidifying the recovered magnesium lactate to lactic acid by bringing said magnesium lactate into contact with said feed comprising hydrogen chloride, thereby forming a liquid effluent comprising lactic acid and magnesium chloride; g) separation of lignin from the liquid effluent product of step f); and, h) separation of the lactic acid and magnesium chloride present in the liquid effluent product of step g) to obtain a lactic acid product stream and a magnesium chloride solution or suspension. Separation step h) might comprise a lactic acid extraction step, by way of example.

The so-separated magnesium chloride solution or suspension (step g)) may then be subjected to a temperature of at least 300° C., thereby decomposing magnesium chloride into magnesium oxide and hydrogen chloride and thus obtaining a solid comprising magnesium oxide and a gas comprising gaseous hydrogen chloride. In turn, the so-derived magnesium oxide might be used directly in at least one of step a) and step c) of the recited method or, alternatively, be used as a precursor for a caustic magnesium salt used in at least one of step a) and step c); as regards the latter possibility, $Mg(OH)_2$ can be obtained by slaking this magnesium oxide, for instance. It is also considered that heat conserved in the solid magnesium oxide from the thermal decomposition of magnesium chloride may be transferred to the lignocellulosic material of step a) and/or the fermentation broth of step c). And still further, the feed comprising hydrogen chloride as used in step e) above may be at least partially derived from gaseous hydrogen chloride obtained from the thermal decomposition of the magnesium chloride.

In several further embodiments, the magnesium lactate may be subjected to a step to convert the magnesium lactate (first lactate salt) to a different lactate salt (second lactate salt). For instance, a magnesium lactate may be subjected to a salt exchange reaction with a monovalent base (e.g., at least one of NaOH, $Na_2CO_3$, $NaHCO_3$, KOH, $K_2CO_3$, $KHCO_3$, $NH_4OH$, $(NH_4)_2CO_3$, and $(NH_4)HCO_3$, preferably NaOH and/or KOH) to form a monovalent lactate salt and magnesium salt (e.g. magnesium hydroxide). See also WO 2005/123647 and WO2010/063762, which are incorporated herein by reference and which describe the production of lactic acid and/or lactate salt from a magnesium lactate comprising medium by a salt exchange reaction between magnesium lactate and a monovalent base. In particular, as described in WO 2005/123647, magnesium lactate may be reacted with the monovalent base at a pH range between 9 and 12, preferably between 9.5 and 11 to form a monovalent lactate salt and magnesium hydroxide.

When a process as described herein is used for preparing lactic acid, the magnesium lactate or the second lactate salt may be converted to lactic acid by an ion exchange method, e.g. by use of an ion exchange column or electrodialysis. The magnesium lactate or second lactate salt may also be acidified with a strong acid (e.g. hydrochloric acid, sulfuric acid and/or nitric acid, preferably hydrochloric acid) as described above to provide a mixture of lactic acid and a magnesium salt. This mixture may be subsequently subjected to a lactic acid/magnesium salt separation step. The magnesium salt may be subjected to a salt splitting step, e.g. a thermal salt splitting step (TSS) as described above. Reference is made to WO 2011/095631, which contents incorporated herein by reference and which describes a process for the preparation of lactic acid. This process comprises subjecting a magnesium lactate to a salt exchange reaction to provide a monovalent lactate salt, and subjecting the monovalent lactate salt to water-splitting electrodialysis, to produce lactic acid.

In several embodiments, the magnesium lactate, second lactate salt or lactic acid obtained as described above may be subjected to at least one of liquid/liquid extraction, nanofiltration, active carbon treatment, distillation and re-crystallization. These treatments may be used to further remove impurities from the magnesium lactate, second lactate salt or lactic acid products.

A lactic acid product obtained by a process as described herein may be in solid form, liquid form or in solution, and may generally comprises at least 95 wt. % of lactic acid, preferably at least 97 wt. % of lactic acid, more preferably at least 99 wt. % of lactic acid, even more preferably at least 99.5 wt. % of lactic acid and most preferably at least 99.9 wt. % of lactic acid.

A lactic acid obtained by a process according to the invention is therefore of high purity and is suitable for direct use in, for example, synthetic processes, food applications and cosmetic applications. A lactic acid obtained as described herein may be especially suited for the preparation of lactide and/or polylactic acid. Any conventional process as known to the person skilled in the art may be used for said manufacture of lactide and/or polylactic acid provided that the starting material containing lactic acid is made via a process as described herein.

Whilst the industrial utility of lactic acid is well known, those impurities originating from the pretreatment, treatment, fermentation and/or isolation steps of a process as described herein may also find utility after appropriate physical and / or chemical processing. It is envisaged that residual cellulose and lignin may serve as boiler fuel for electricity or steam production. Further, black liquor gasification of lignin is a recent commercial development. Certain impurities may be used as fertilizer, particularly magnesium rich fertilizer. And carbon dioxide released in the fermentation process may be captured for sale, for example, to the beverage industry.

The present invention is further illustrated by the following Example, without being limited thereto or thereby.

EXAMPLES

Raw Materials and Their Analysis:

Bagasse was provided by Purac Thailand Ltd. (Rayong, Thailand).

Ground wheat straw was obtained from a local supplier. For Examples 1 to 9 below, the wheat straw was milled using a Retch Cutting Mill (SM100) and then screened to attain a median particle size in the range from 500 microns to 1 mm. For Example 10 below, the wheat straw was milled using hammer mill (Apex Commuting Mill) with a screen size of 1.5 mm.

Using a Mettler Toledo Advanced Moisture Analyzer, the dry weight contents of selected 0.5-2.0 g milled wheat straw samples were measured.

The wheat straw and bagasse were analyzed for carbohydrate, acid soluble lignin, acid insoluble lignin and ash contents in accordance with the procedure given in: *Determination of Structural Carbohydrates and Lignin in Biomass: Laboratory Analytical Procedure* (LAP), National Renewable Energy Authority (August 2012) http://www.n-rel.qov/docs/gen/fv13/42618.pdf; and, Determination of Ash in Biomass: Laboratory Analytical Procedure (LAP), National Renewable Energy Authority (January 2008) http://www.nrel.gov/docs/gen/fy08/42622.pdf. Where applicable, current practice relating to said procedures may be found at http://www.nrel.qov/biomass/analytical procedures.html.

Where applicable, glucose was determined using the Megazyme D-Glucose assay kit (glucose oxidase/peroxidase; GOPOD) employing a pulsed amperometric detector (Roche/Hitachi GOD-PAD) and spectrophotometry (Hitachi U-2800, 540 nm). Xylose may be determined using the Megazyme D-xylose kit and spectrophotometry (Hitachi U-2800, 340 nm).

The theoretical maximum yield of glucose from wheat straw was determined to be 37.1 wt. %, based on the total dry weight.

Examples 1-9

Pre-Treatment: Weighed 12.45 g portions of the milled wheat straw or bagasse were separately slurried in 150 mIdemineralised water, following which the solid magnesium oxide or, where applicable, solid calcium oxide or sodium hydroxide were added thereto; no further basic compounds were added. For completeness, it is noted that in Example 9 below, the NaOH was added to the milled wheat straw after the solid magnesium oxide, thereby raising the pH of that sample.

The pre-treatment of said samples was carried out in a double wall stainless steel, stirred reactor (Buchi Autoclave). The reactor was rated for 60 Bar and was equipped with a pressure safety spring. Heating was carried out using hot oil up to 190° C.

The properties of each separate portion and the different conditions of temperature and residence time to which they were subjected are shown in Table 1 herein-below. All samples were continuously stirred for the requisite residence time in the reactor. Further all samples that were treated with caustic magnesium or calcium oxide had an initial pH of from 8.5-9.4 prior to any heating step.

Preparation for Enzymatic Hydrolysis: The thus pre-treated solids were subjected to a first solid/liquid separation step using a Buchner filter under reduced pressure (approx. 200 mBar). The liquid fraction was collected for analysis. The solids were collected, dispersed in water and neutralized to a pH of from 6-7 with lactic acid.

Next the solids were subjected to a two-stage second solid / liquid separation step using a filtering centrifuge (Hermle Sieva 2) equipped with a 5 micron filter cloth. In a first stage, the centrifuge is initiated at 5000 rpm before being increased to 10000 rpm; the filtrate is collected and added to the centrifuge again; samples of the then derived filtrate and filter cake are collected for analysis. In a second stage, the centrifuge is re-initiated with the addition of 1 liter of demineralized water thereto. The separated solid fraction was then collected; its dry matter content was measured before being subjected to enzymatic hydrolysis.

Enzymatic Hydrolysis: At a dry matter content of 10% (w/w), the pre-treated solids were hydrolyzed in 50 mL polypropylene tubes with a cellulase enzyme mix CMAX4 available from Dyadic. A potassium phosphate buffer (pH, 6.4) was employed and, furthermore, sodium azide (0.02%, w/w) was present to prevent microbial infection of the hydrolyzate. The added amount of enzyme was varied in the experiments—as indicated in Table 1—with enzyme loading of 20 mg/g dry weight being more usual, noting that this loading should ensure satisfactory release of carbohydrates (NREL, 2011).

The hydrolyzation reactions were incubated at 52° C. at 300 rpm. After 24 hours, 48 hours and 72 hours, duplicate 0.2 ml samples were taken and filtered using a micro plate; the duplicate supernatants were then analyzed.

The concentrations of glucose are given in Table 1 below,

Example 10

This Example is intended to demonstrate the scaling up of the pre-treatment process to accommodate larger amounts of lignocellulosic material.

Pre-Treatment: Weighed 1.6 kg portions of the milled wheat straw were separately slurried in 13.4 liters of demineralised water, following which the solid magnesium oxide was added thereto; no further basic compounds were added.

The pre-treatment of said samples was carried out in a double wall stainless steel, jacketed reactor equipped with an anchor propeller (50 liter Buchi Autoclave). The reactor was rated for at least 20 Bar and was equipped with a pressure safety spring. Heating to 190° C. was carried out using both direct injection of pressurized steam and hot oil circulated through the jacket. The reaction mixture was stirred continuously during its residence time in the reactor.

After the reaction was performed, the reactor was cooled using oil circulated in the jacket followed by a rapid cooling effected by releasing the pressure of the reactor. The contents of the reactor were then collected.

The properties of the collected material and the conditions of temperature and residence time to which that material had been subjected are shown in Table 2 herein-below. Further the samples that were treated with caustic magnesium oxide in this manner had an initial pH of from 8.5-9.4 prior to any heating step.

Preparation for Enzymatic Hydrolysis: The thus pre-treated solids were subjected to a first solid/liquid separation step under gravity using a 1 mm screen, the liquid fraction being collected in a 120 liter vessel. The solids were collected, dispersed in water in a further 120 liter vessel and neutralized to a pH of from 6-7 with lactic acid (50 wt. % aqueous solution).

TABLE 1

| Example | Substrate | Pre-Washed (Y/N) | Treatment Temp. (° C.) | Residence Time (min.) | Alkaline Agent | Alkaline Agent Dosage (% w/w) | Enzyme dosage (mg protein/g dry solids) | Glucose concentration (g/L, at 72 h) |
|---|---|---|---|---|---|---|---|---|
| 1 | Milled Wheat straw | Y | 190 | 60 | MgO | 12 | 5 | 23.3 |
| 2 | Milled Wheat straw | Y | 190 | 120 | MgO | 12 | 5 | 14.9 |
| 3 | Milled Wheat straw | Y | 190 | 60 | MgO | 8 | 5 | 18.1 |
| 4 | Milled Wheat straw | Y | 190 | 120 | MgO | 8 | 5 | 13.0 |
| 5 | Milled Wheat straw | Y | 190 | 60 | MgO | 10 | 20 | 40.6 |
| 6 | Milled Wheat straw | N | 190 | 60 | MgO | 10 | 20 | 37.5 |
| 7 | Milled Wheat straw | Y | 190 | 30 | MgO | 10 | 20 | 37.2 |
| 8 (Comparative) | Milled Wheat straw | Y | 85 | 480 | CaO | 8 | 20 | 22.9 |
| 9 | Bagasse | Y | 190 | 20 | MgO + NaOH (pH = 11) | 10 | 20 | 13.7 |

The slurry formed was again filtered under gravity as described above (1 mm screen) except that 26 liters of demineralized water was sprinkled evenly over the filter cake. The filter cake was divided into six portions (SHFPs) each of which was pressed at an applied pressure of 250 Bar using a bench press filter (Fischer MachineFabriek). Each separated solid fraction was then collected; the cakes were subsequently broken up, homogenized and distributed over two containers (SHFP1, SHFP2); the dry matter content of each container was measured and found to be from 38-42% (w/w).

Enzymatic Hydrolysis: The pre-treated solids (SHFP1) were hydrolyzed in polypropylene tubes with a cellulase enzyme mix CMAX4 available from Dyadic; the pre-treated solids were added so as to be in an amount of 10 wt. %, by dry weight (c. 1 g dry weight). A potassium phosphate buffer (pH, 6.4) was employed and, furthermore, sodium azide (0.02%, w/w) was present to prevent microbial infection of the hydrolyzate. The enzyme loading was 20 mg/g dry weight.

The hydrolyzation reactions were incubated at 52° C. at 300 rpm. After 24 hours and 48 hours, duplicate 0.2 ml samples were taken and filtered using a micro plate; the duplicate supernatants were then analyzed. The concentration of glucose after 48 hours is given in Table 2 below.

hours. The pH of the medium was also maintained at 6.4 during this period by the addition of magnesium hydroxide (20 wt. % aqueous solution) thereto.

The inoculated medium was then added to the adapted minifors unit. The medium was stirred at 200 rpm and maintained at a temperature of 52° C. The pH of the medium was also maintained at 6.4 during this period by the addition of magnesium hydroxide (aqueous solution) thereto.

25 ml samples of the supernatant were taken regularly, on average every 3 hours, and used to determine the concentration of glucose, xylose and lactic acid, lactic acid concentration being determined using HPLC. Measurements were stopped at 48 hours total time when the concentration of both glucose and xylose was less than 0.3 g/L. The final concentration of lactic acid is shown in Table 3 below.

TABLE 3

| Ex. | *Initial glucose concentration start fermentation (g/L) | *Initial xylose concentration start fermentation (g/L) | Fermentation (hours) | Final lactic acid concentration (g/L) |
|---|---|---|---|---|
| 11 | 40.6 | 10.7 | 47.9 | 58.3 |

*Initial concentration is measured in the hydrolysate after dilution and before addition of the seed fermentation.

TABLE 2

| Example | Substrate | Treatment Temp. (° C.) | Residence Time (min.) | Alkaline Agent | Alkaline Agent Dosage (% w/w) | Enzyme dosage (mg protein/g dry solids) | Glucose concentration (g/L, at 48 h) |
|---|---|---|---|---|---|---|---|
| 10 | Milled Wheat straw | 190 | 59 | MgO | 10 | 20 | 53.2 |

Example 11

Enzymatic Hydrolysis: The pre-treated solids (SHFP2) were hydrolyzed in a minifors unit adapted to include a high torque, helical stirrer. Hydrolysis was performed with a cellulase enzyme mix CMAX4 available from Dyadic; the pre-treated solids were added so as to be in an amount of 15 wt. %, by dry weight. The enzyme loading was 30 mg/g dry weight.

The hydrolyzation reactions were incubated at 52° C. at 200 rpm for 48 hours; the hydrolysate (H1), having a glucose concentration of 76 g/L, was harvested by centrifugation. The hydrolyzate was collected into the adapted Minifors unit, diluted with demineralized water (1:1 ratio) and then maintained at 80° C. for 30 minutes for pasteurization. The unit is then cooled to the desired fermentation temperature of between 50° C. and 54° C.

Fermentation: As used in this Example, *Bacillus coagulans* DSM2314 is a publically available, non-GMO strain. A work stock of *Bacillus coagulans* DSM2314 was taken from a -80° C. freezer and pre-cultured in a sterile medium containing 7.7 g/l dextrose monohydrate, 2 g/l DAP, 3.5g/l DAS, 1 g/l CaCl$_2$.5H$_2$O, and 10 g/l yeast extract paste (50% Dry Solids).

Seed Fermentation: To generate a seed fermentation, a standard Minifors unit was loaded with 1 liter of said sterile fermentation medium. To this medium was added 50 ml of the above inoculum. The medium was stirred at 200 rpm and maintained at a temperature of 52° C. for approximately 20

Figure 1:
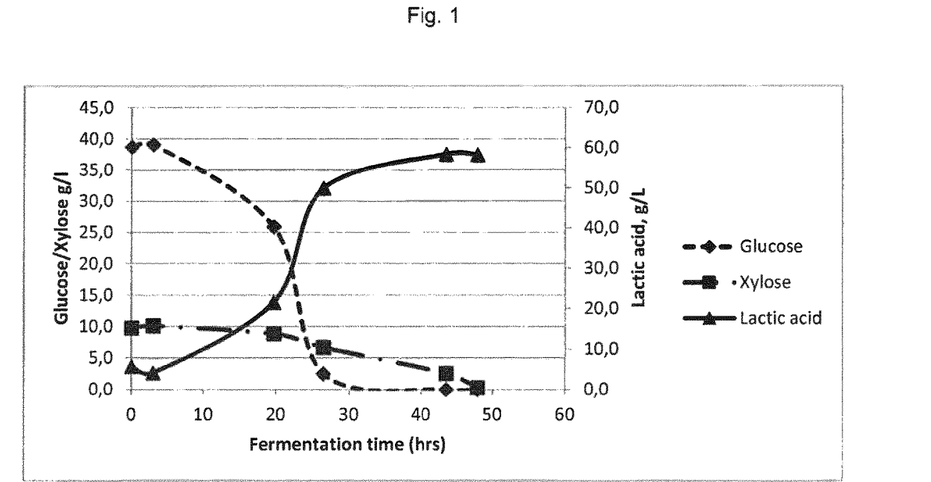
FIG. 1 illustrates the change in concentration of glucose, xylose and lactic acid over time during separate fermentation according to embodiments of the present application.

FIG. 1 appended hereto illustrates the change in concentration of glucose, xylose and lactic acid over time during the separate fermentation.

Figure 2:
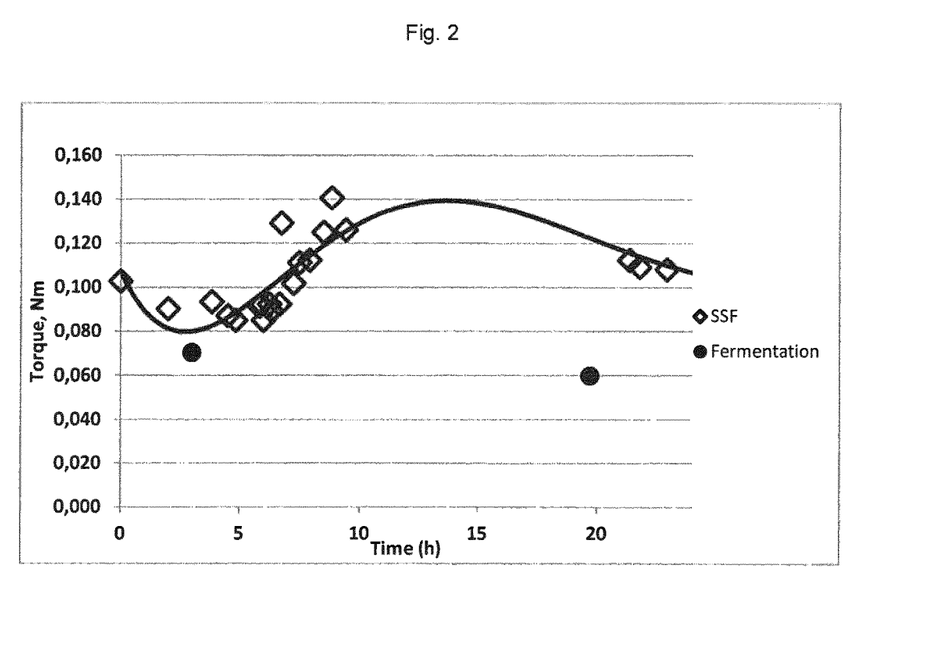
FIG. 2 illustrates a comparison of torque measurements, as applied to the helical stirrer of an adapted Minifors unit, for both separate hydrolysis and fermentation according to the present application a comparative process of simultaneous hydrolysis and fermentation.

Torque measurements, as applied to the helical stirrer of the adapted Minifors unit, were made throughout the course of the separate hydrolysis and fermentation and data points thereof are shown in FIG. 2 appended hereto. The line of this Figure is derived from a polynomial regression of the obtained data points.

Reference Example 12

Torque measurements were also performed during a simultaneous saccharification and fermentation process as defined below.

Pre-Treatment: Weighed 1.6 kg portions of the milled wheat straw were pre-treated in an identical manner to that described for Example 10 above. The properties of the collected material and the conditions of temperature and residence time to which that material had been subjected are thus shown in Table 2 herein-above. Further, as previously the samples that were treated with caustic magnesium oxide in this manner had an initial pH of from 8.5-9.4 prior to any reactor heating step.

Preparation for Simultaneous Saccharification and Fermentation: The thus pre-treated solids were subjected to a first solid/liquid separation step under gravity using a 1mm screen, the liquid fraction being collected in a 120 liter vessel. The filter cake was divided into 11 portions (SSFPs)

each of which was pressed at an applied pressure of 250 Bar using a bench press filter (Fischer MachineFabriek). Each separated solid fraction was then collected; the cakes were subsequently broken up, homogenized and distributed over two containers (SSF1, SSF2). An averaged dry matter content of each container was measured as: 40.26% w/w, SSF1; and, 42.95% w/w, SSF2.

Simultaneous Saccharification and Fermentation

As used in this Example, *Bacillus coagulans* DSM2314 is a publically available, non-GMO strain. A work stock of *Bacillus coagulans* DSM2314 was taken from a −80° C. freezer and pre-cultured in a sterile medium containing 7.7 g/l dextrose monohydrate, 2 g/l DAP, 3.5 g/l DAS, 1 g/l $CaCl_2 \cdot 5H_2O$, and 10 g/l yeast extract paste (50% Dry Solids).

Seed Fermentation: To generate a seed fermentation, a standard Minifors unit was loaded with 1 liter of said sterile fermentation medium. To this medium was added 50 ml of the above inoculum. The medium was stirred at 200 rpm and maintained at a temperature of 52° C. for approximately 20 hours. The pH of the medium was also maintained at 6.4 during this period by the addition of magnesium hydroxide (aqueous solution) thereto.

The simultaneous saccharification and fermentation was performed in a further minifors unit adapted to include a high torque, helical stirrer and an external 1 rpm pump for the addition of sludge to said unit.

In this Example, a two hour pre-saccharification step was employed, whereby the substrate (SSF1) was first loaded into the adapted minifors unit in the absence of the inoculum at a substrate loading of 5% (w/w) dry matter. The pre-saccharification was performed with cellulase enzyme mix CMAX4 (Dyadic) at an enzyme loading of 20 mg/g dry weight; at a start volume of 1300 ml, the pre-saccharification medium was stirred at 200 rpm and maintained at a temperature of 52° C. and a pH of 6-7.

After two hours, 100 ml of the inoculum was introduced and the reactor maintained at the above conditions of stirring, temperature and pH for a further 3 hours, again using magnesium hydroxide to control the pH.

Following this, the stirrer was stopped and first 50g dosage of substrate (SSF1) introduced; the stirrer was then re-started to 200 rpm and the temperature of the reactor moderated to 52° C., if required. The pH was monitored and further 50 g dosages of substrate added in the same manner when the pH of the medium fell below 6.4. Such substrate addition was continued until the content of the reactor was approximately 20% (w/w) dry matter.

Torque measurements, as applied to the helical stirrer of the adapted Minifors unit, were made throughout the course of the SSF and are also shown in FIG. 2 appended hereto. Measurements were stopped at c. 24 hours total time (pre-saccharification plus SSF time).

It will be apparent to those skilled in the art, upon consideration of the specification that various modifications can be made in the disclosed embodiments without departing from the scope of the invention. It is therefore intended that the embodiments and examples be considered illustrative only, with the true scope of the invention being indicated by the following claims.

The invention claimed is:

1. A process for preparing lactic acid and/or a lactate salt comprising:
   a) treating a lignocellulosic material with an alkaline agent comprising a caustic magnesium salt in the presence of water to provide a treated aqueous lignocellulosic material;
   b) saccharifying the treated aqueous lignocellulosic material in the presence of a hydrolytic enzyme to provide a saccharified aqueous lignocellulosic material comprising fermentable carbohydrates and a solid lignocellulosic fraction;
   c) fermenting the fermentable carbohydrates in the saccharified aqueous lignocellulosic material by means of a lactic acid producing microorganism in the presence of an alkaline agent comprising a caustic magnesium salt to provide an aqueous fermentation broth comprising a magnesium salt of lactic acid; and,
   d) isolating lactic acid and/or a salt of lactic acid from the fermentation broth,
   wherein the saccharification step b) and the fermentation step c) are performed as two separate steps.

2. The process according to claim 1 comprising subjecting the lignocellulosic material to at least one of acid treatment, solvent treatment and steam treatment prior to treating the lignocellulosic material with the alkaline agent of step a).

3. The process according to claim 1 comprising treating the lignocellulosic material with the alkaline agent of step a)
   i) at a pH from 4.0 to 14.0;
   ii) at a temperature from 15 to 250° C. and,
   iii) for a time period of from 1 minute to 600 minutes.

4. The process according to claim 1 comprising subjecting the lignocellulosic material to acid treatment prior to treating said material with the alkaline agent of step a),
   wherein said acid treatment comprises mixing said lignocellulosic material with an acidic aqueous solution having a concentration of 8 wt.% or less of acid selected from the group consisting of inorganic acid, organic acid, amino acid, mineral acid, Bronsted acid, Lewis acid and mixtures thereof, and
   wherein said mixing takes place at a temperature of from 120° C. to 230° C.

5. The process according to claim 4, wherein the treatment of step a) is performed
   i) at a pH of from 2 to 10.
   ii) at a temperature of from 15 to 100° C.
   iii) for a period of from 1 to 30 minutes, to neutralize the acid treated lignocellulosic material.

6. The process according to claim 1 comprising performing the saccharification of step b) and/or the fermentation of step c)
   i) at a pH from 2.0 to 10.0; and
   ii) at a temperature from 30 to 80° C.

7. The process according to claim 1 comprising performing the saccharification of step b)
   i) at a at a pH from 4.5 to 5.5; and
   ii) at a temperature from 50 to 60° C.

8. The process according to claim 1 comprising adjusting the pH of the treated aqueous lignocellulosic material of step a) by acidification prior to the saccharification of step b), wherein acidification is performed with lactic acid.

9. The process according to claim 1 comprising subjecting the saccharified aqueous lignocellulosic material to a solid/liquid separation step prior to the fermentation of step c) to remove the solid lignocellulosic fraction from the saccharified lignocellulosic material comprising the fermentable carbohydrates.

10. The process according to claim 1 comprising subjecting the saccharified aqueous lignocellulosic material to a concentration step and/or a detoxification step prior to the fermentation of step c).

11. The process according to claim 1 comprising fermenting the saccharified aqueous lignocellulosic material
   i) at a pH from 5.5 to 7.5, and
   ii) at a temperature from 50 to 60° C.

12. The process of claim 1, wherein in step d) magnesium lactate is isolated from the fermentation broth.

13. The process of claim 1, wherein magnesium lactate is treated with an acid, selected from the group consisting of hydrochloric acid, sulphuric acid, and nitric acid.

14. The process of claim 13, which comprises the steps of e) providing a feed comprising hydrogen chloride, said feed being either an aqueous solution comprising hydrogen chloride or a gas feed comprising gaseous hydrogen chloride; f) acidifying the recovered magnesium lactate to lactic acid by bringing said magnesium lactate into contact with said feed comprising hydrogen chloride, thereby forming a liquid effluent comprising lactic acid and magnesium chloride; g) separation of lignin from the liquid effluent product of step f); and, h) separation of the lactic acid and magnesium chloride present in the liquid effluent product of step g) to obtain a lactic acid product stream and a magnesium chloride solution or suspension.

15. The process of claim 1, where the magnesium lactate is converted to a further lactate salt through a salt exchange process.

16. The process of claim 1, wherein the magnesium lactate, further lactate salt, or lactic acid are subjected to one or more of liquid/liquid extraction, nanofiltration/active carbon treatment, distillation, and recrystallization.

17. The process of claim 1, where prior to the fermentation step, the solid lignocellulosic fraction is removed.

* * * * *